United States Patent [19]
Ghosal

[11] Patent Number: 6,124,268
[45] Date of Patent: Sep. 26, 2000

[54] NATURAL ANTIOXIDANT COMPOSITIONS, METHOD FOR OBTAINING SAME AND COSMETIC, PHARMACEUTICAL AND NUTRITIONAL FORMULATIONS THEREOF

[75] Inventor: Shibnath Ghosal, Varanasi, India

[73] Assignee: Natreon Inc., Highland Park, N.J.

[21] Appl. No.: 09/251,917

[22] Filed: Feb. 17, 1999

[51] Int. Cl.$^7$ .................................................. A01N 65/00
[52] U.S. Cl. .............................. 514/27; 514/25; 424/401; 424/439; 424/440; 424/195.1
[58] Field of Search .................................... 424/401, 439, 424/440, 195.1; 514/25, 27

[56] References Cited

PUBLICATIONS

"Active Constituents of Emblica officinalis: Part 1—The Chemistry and Antioxidative Effects of Two New Hydrolysable Tannins, Emblicanin A and B", Shibnath Ghosal et al. Indian Journal of Chemistry vol. 35B, Sep. 1996, pp. 941–948.

*Primary Examiner*—Frederick Krass
*Attorney, Agent, or Firm*—Walter Katz

[57] ABSTRACT

A natural antioxidant blend in the form of an amphorous powder was obtained by extraction from *Emblica officinalis* fruit. In this process, the finely pulped fruit was treated with a dilute aqueous salt solution at hot water temperature to provide an extract-containing solution, which was filtered and dried to provide the desired antioxidant blend powder. Cosmetic, pharmaceutical and nutritional use formulations thereof also are described.

13 Claims, No Drawings

NATURAL ANTIOXIDANT COMPOSITIONS, METHOD FOR OBTAINING SAME AND COSMETIC, PHARMACEUTICAL AND NUTRITIONAL FORMULATIONS THEREOF

BACKGROUND OF THE INVENTION

1. Field of the Invention

The present invention relates to an enriched natural anti-oxidative blend in the form of an amorphous powder, and, more particularly to a process for obtaining such blend by an extraction process from *Emblica officinalis* fruit, which has advantageous antioxidant and free radical captodative properties, and cosmetic, pharmaceutical and nutritional use compositions thereof, particularly for protection of the skin against the sun and its damaging ultraviolet radiation.

2. Description of the Prior Art

As it is well known, L-ascorbic acid (vitamin C) is a naturally-occurring compound found in many fruits and vegetables. L-ascorbic acid functions in many biological processes such as collagen synthesis, anti-oxidation, intestinal absorption of iron and metabolism of some amino acids. An essential function of L-ascorbic acid in these processes is to act as a cofactor for the hydroxylation of proline and lysine residues in collagen, a major protein component of the body. L-ascorbic acid also increases the transcription rate of procollagen genes and stabilizes pro-collagen mRNA. Its well-known ability to cure scurvy, for example, may be also due to the stimulation of collagen synthesis in connective tissues.

While ascorbic acid possesses many indispensable biological properties, it has several disadvantages. For example, it is susceptible to air oxidation and sensitive to heat, and is unstable in aqueous solution, even under neutral pH and at room temperature. To solve these problems, the art has stabilized ascorbic acid by complexation with cyclodextrin, zeolites or liposomes. Another approach consists of stabilizing ascorbic acid by derivatization of its ene-diol function at the 2-position, for example, as L-ascorbic acid 2-phosphate or L-ascorbic acid 2-sulfate. The ascorbic acid 2-phosphate derivative does show some biological activity, however, ascorbic acid 2-sulfate is no longer an effective biological agent.

The provision of a stable ester at the 2-position of ascorbic acid also has been proposed. Monoalkyl esters having 1 to 18 carbon atoms, fluoroalkyl esters having 2 to 7 carbons and from 4 to 15 atoms of fluorine, and substituted benzoyl or cinnamate esters have been prepared for this purpose.

It is important to note that ascorbic acid can react with metal ions, such as iron and copper to yield active oxygen species and may act as a dangerous prooxidant [(B. Halliwell, *Free Radical Research*, 25, 439–54 (1996)].

SUMMARY OF THE INVENTION

Accordingly, an object of this invention is to provide a natural antioxidant composition or blend having enriched antioxidant and free radical. Captodative properties, a process for obtaining such blends, and cosmetic, pharmaceutical and nutritional use formulations thereof, particularly for protection of skin against the damaging effects of the sun.

These and other objects and features of the invention will be made apparent from the following more detailed description.

It has now been found, surprisingly, that the anti-oxidative fraction of *Emblica officinalis*, a member of small genus of Emblica trees, which are native to India, Sri Lanka, Malaysia and China, is much more stable under self-oxidation than L-ascorbic acid itself and some of its derivatives described in the literature. S. Ghosal et al, Indian J. of Chem. 35B, Sep. 1996, pgs 941–948. Moreover, it has been found, unexpectedly, that the compounds according to this invention have much better anti-oxidative properties against reactive oxygen species and can stabilize and prolong the anti-oxidative properties of ascorbic acid.

The major advantage of the anti-oxidative product of this invention is its enhanced stability in an aqueous environment when compared with ascorbic acid or even magnesium ascorbyl phosphate. The product of this invention also contains low to medium molecular weight tannoids which augments its resultant anti-oxidant properties.

In addition to its anti-oxidative activity, the product herein can be formulated to provide significant protection against UV-induced erythema, particularly, by at least 50% when compared with a placebo formulation.

The anti-oxidant product of the invention (referred to hereinafter as "CAPROS") is isolated in stable form from the fruit of *Emblica officinalis* plant using a very dilute aqueous or alcoholic water salt solution, e.g. a 0.1 to 5% (w/w), preferably 1 to 2%, of a sodium chloride, potassium chloride, calcium chloride or magnesium chloride solution, which prevents degradation of the anti-oxidant compounds therein by enzymes present in the fruits of the *Emblica officinalis* plant. Alternately, the antioxidant product is isolated using buffer solution, e.g. 0.1 to 5% (w/w), preferably 1 to 2%, of sodium citrate/citric acid, sodium acetate/acetic acid, sodium phosphate/phosphoric acid, instead of aqueous or alcoholic water salt solution.

The antioxidant composition of the invention provides advantageous cosmetic, pharmaceutical and nutritional compositions, generally at a use level of the invention compositions of from about a 0.05 to about 10% by weight.

The anti-oxidant composition of this invention contains, by weight, Em-A and B (gallic/ellagic acid derivatives of 2-keto-glucono-δ-lactone) (35–55%), Punigluconin (2,3-di-O-galloyl-4,6-(S)-hexahydroxy-diphenoylgluconic acid) (4–15%), Pedunculagin (2,3,4,6-bis-(S)-hexahydroxydiphenoyl-D-glucose) (10–20%); Rutin (flavanol-3-)glycoside (5–15%); and low to medium molecular weight gallo-ellagi tannoids (10–30%).

STRUCTURES OF THE CHEMICAL CONSTITUENTS OF CAPROS™

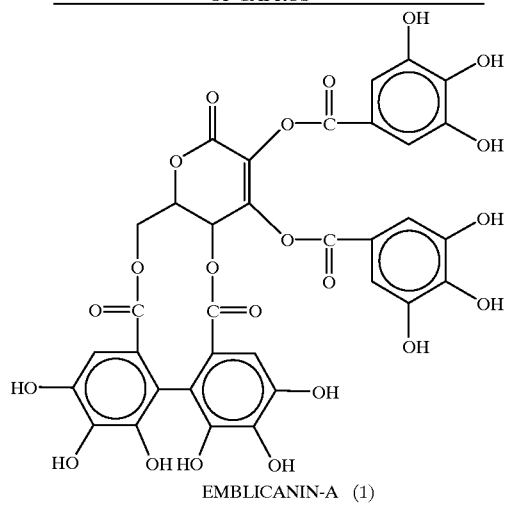

EMBLICANIN-A (1)

-continued

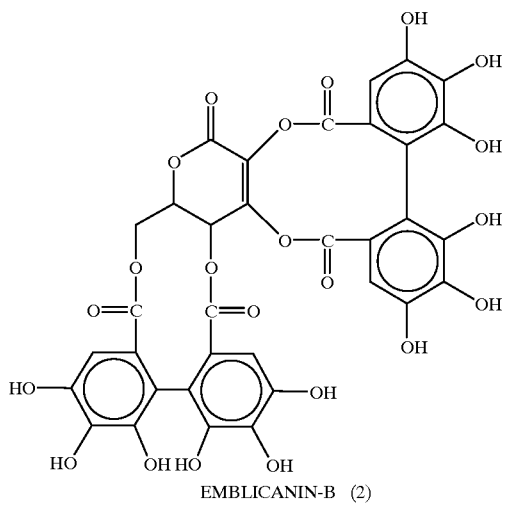

EMBLICANIN-B (2)

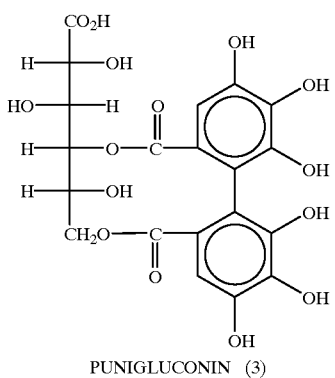

PUNIGLUCONIN (3)

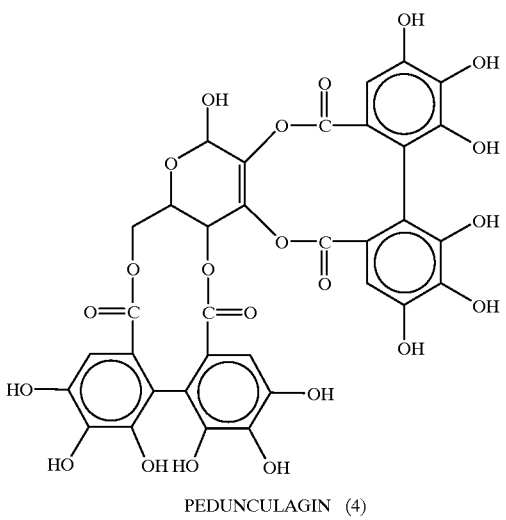

PEDUNCULAGIN (4)

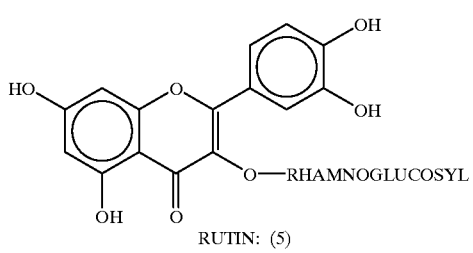

RUTIN: (5)

DETAILED DESCRIPTION OF THE INVENTION

Small tannoids of the gallo-ellagi tannins class couple with reductones like 2-keto-gluconolactone (and equivalents) to produce Emblicanin-A and Emblicanin-B, and other related tannoids of low molecular weight, which act as potent antioxidative and free radical captodative agents. The free radical chain-breaking process takes place more efficiently by CAPROS than the combination of ascorbic acid and vitamin E. In the presence of Rutin, a synergistic antioxidative-radical captodative effect was observed for the constituents in CAPROS.

A simple and efficient method of extracting, concentrating and preserving CAPROS, present in the fresh fruits of *Emblica officinalis* (Hindi, Amla), is described hereinafter.

This CAPROS extraction, concentration and preservation process results in the destruction of the native hydrolytic enzymes, e.g. glycosidases, present in the fresh fruits of Amla. The destruction of the glycosidic enzymes is achieved herein by heating the fresh fruit pulp in water containing, for example, 1% NaCl (w/w), for 1 hour on a steam bath at $70°±5°$ C. The mixture is then filtered, refrigerated for 3 days, and spray-dried or, alternatively, vacuum dried. The presence of NaCl in the extraction medium prevent hyrolysis by the glycosidic enzymes in the plant, and, also, to protect the product from microbial infestation.

Several varieties of Amla, collected from certain regions in India, and at a predetermined time of harvesting, contain a relative abundance of Emblicanin-A and B, and their equivalents, and these compounds are isolated during the process of the invention. The CAPROS product obtained thereby can be used directly as a potent antioxidative and free radical captodative agent, or enriched further by subsequent chromatography.

The increased concentration of these agents in the composition of the invention is a result of the defined extraction process which prevents degradation of the small gallo-ellagi tannoids, coupled with the reductones, by native enzymes present in the plant. The present process enables isolation and enrichment of these bioactive compounds, viz. Emblicanin-A and Emblicanin-B, and two medium molecular weight gallo-ellagi tannins, from the fresh pericarp of *Emblica officinalis* Linn (Euphorbiaceae). The enriched Emblicanin-A and -B fractions in association with the minor congener compounds, —Punigluconin and Pedunculagin (both medium $M_w$ gallo-ellagi tannins), and Rutin (a flavonol glycoside), present in the berries, constitute a well-defined composite antioxidative mixture having oxygen radical captodative properties which are at least 3 times higher than Vitamin C.

A liposomic complex gel, prepared by combining CAPROS and a lecithin, provides protection against UV radiation-induced erythema.

Composition of CAPROS

The chemical compounds present in a representative sampling of the product of the invention comprise: (1) Emblicanin-A (27%); (2) Emblicanin-B (23%); (2) Punigluconin (8%); (4) Pedunculagin (14%); (5) Rutin (10%); and (6) gallo-ellagitannoids (10–30%).

Source material: *Emblica officinalis*, pericarp of fresh berries.

Appearance of CAPROS: brown hygroscopic powder; 0.1% aq. solution, light-yellow in color.

Odor: weak characteristic odor.

Solubility: freely soluble in water; peracetates of CAPROS soluble in aprotic solvents (toluene, diethyl ether).

Identification: by HPTLC [CAMAG TLC evaluation software (Scanner III); developing solvent, Ethyl acetate-acetic acid-formic acid-water (100:11:11:27); detection, absorption/quenching mode, λ max 254 nm]. Stability: antioxidative and radical captodative properties remain unchanged for over 1 year.

The Constituents

1. Emblicanin-A: 2,3-di-O-galloyl-4,6-(S)-hexahydroxydiphenoyl-2-keto-glucono-lactone (str. 1); yellowish-grey amorphous powder (hygroscopic), $C_{34}H_{22}O_{22} \cdot 2H_2O$
2. Emblicanin-B: 2,3,4,6-bis-(S)-hexahydroxydiphenoyl-2-keto-glucono-lactone (str. 2); tan colored (hygroscopic powder), $C_{34}H_{20}O_{22} \cdot 2H_2O$
3. Punigluconin: 2,3-di-O-galloyl-4,6-(S)-hexahydroxydiphenoyl gluconic acid (str. 3); grey amorphous powder (hygroscopic), $C_{34}H_{26}O_{23} \cdot 2H_2O$
4. Pedunculagin: 2,3,4,6-bis-(S)-hexahydroxydiphenoyl-D-glucose (str. 4); tan (hygroscopic) powder; $C_{34}H_{24}O_{23} \cdot 2H_2O$
5. Rutin: 3',4',5,7-tetrahydroxyflavono-1,3-O-rhamnoglucoside (str. 5); light yellow powder (free flowing).
6. Gallo-ellagitannoids These compounds were identified by spectroscopic analyses (UV, FT-IR, $^1H$ NMR, FAB-MS) and chemical degradation. Compounds 1 and 2 are new gallo-ellagi tannins, isolated from *E. officinalis* and named herein. Compounds 3, 4 and 5 have been obtained from other plant sources, but isolated for the first time from *Emblica officinalis*.

Biological Actions of CAPROS

Aqueous solution (0.1%) of CAPROS prevents or markedly retard the oxidation of Vitamin C (L-ascorbic acid). The per se antiascorbic activity of CAPROS is preserved in dilute aqueous NaCl solution over a long period of time. Thus, 1% Aq. NaCl solution of CAPROS (0.1%) preserves its vitamin-C like activity of up to 50% of its original value when kept covered, at ordinary temperatures, for over 3 months. Peracetates of CAPROS (at a 1% level) markedly inhibit peroxide development in coconut oil when tested by the swift stability procedure at 90° C. and also by HPTLC analysis. The generation of lipid peroxides by (a) ferrous ion-ascorbate and (b) ferric ion-ADP-ascorbate, in rat liver homogenates, was inhibited to 50% by a 1:1 combination of Emblicanin-A/-B in the dose of 10 mcg/ml in case of (a) and 60 mcg/ml in case of (b). Under similar conditions, the dose of Punigluconin required was 168 mcg/ml for (a) and 194 for (b); while for Pedunculagin, the dose was 174 mcg/ml and 210 mcg/ml, respectively. The free radical scavenging effect of Rutin did not affect this parameter. However, interestingly, a combination of Emblicanin-A (14 mcg) and -B (12 mcg), Punigluconin (5 mcg), Pedunculagin (8 mcg) and Rutin (4 mcg), in a 1 ml solution, completely prevented lipid peroxidation in both the (a) and (b) systems. Hence, the composition of CAPROS is an ideal one for antioxidative and free radical captodative purposes.

Protection from UV Radiation

This functionality test (UV-erythema) for CAPROS was carried out under controlled conditions. Human volunteers (5) were treated, immediately after a 4 min. radiation at 1.5 Rad, with a gel containing 0.5% of CAPROS-lecithin (1:1) complex, this complex is named Emblisome; prepared by intimately mixing 1 mM of CAPROS (average mol. wt 750) with a lecithin, e.g. 1-O-palmitoyl-2-O-stearoyl phosphatidylcholine, (isolated from a plant source) in peroxide-free ether or toluene. The formation of the complex was established by spectroscopic analysis.

Acute toxicity Graded doses (100–1000 mg/kg), orally (p.o.) or intraperitoneally (i.p.), of CAPROS were administered to groups of 10 mice for each dose and the $LD_{50}$ of the compound was tested. No death was observed up to 24 hours when the drug was administered p.o. The $LD_{50}$ by the i.p. route was 814±56 mg/kg. The acute toxicity of CAPROS is therefore of a very low order, and there is a wide safety margin even if it is systemically used for a prolonged period of time.

The invention will now be described in more detail with references to the following examples.

EXAMPLE 1

Fresh *Emblica officinalis* fruit (5 kg) was finely pulped and mixed with water (2-1), containing sodium chloride (1% w/w). The mixture was left standing at room temperature for about 12 hours. Then the mixture was stored in the cold (10° C.) for 3 days. Thereafter it was filtered through a thin cloth and the filtrate was spray-dried. The antioxidant fraction in the spray-dried blend was about 0.1 g/100 g of pulp as determined by high pressure thin layer chromatography (HPTLC). Some free gallic acid (1.8 g/100 g of pulp), and monosaccharides and starches (glucose, rhamnose, galactose, etc.) (12 g/100 g of pulp) also was present in the blend.

EXAMPLE 2

Example 1 was repeated except that the mixture of *Emblica officinalis* fruit and aqueous sodium chloride solution was immediately kept in the cold for 3 days. The spray-dried blend showed a much higher concentration of the antioxidative fraction (1.8 g/100 g of pulp, HPTLC) than obtained in Example 1. The relative abundance of the gallic/ellagic acid derivatives of 2-keto-glucono-δ-lactone in this product was about 25–30% by weight. The remaining components were starches, monosaccharides, free gallic acid and other tannoids.

EXAMPLE 3

*Emblica officinalis* fruit (5 kg) was mixed with hot water (2-1, 70–75° C.) containing sodium chloride (1%, w/w), and maintained for about an hour. The heated mixture was filtered and the filtrate at room temperature was refrigerated for 3 days, re-filtered and the re-filtrate was spray-dried to provide a pale-brown hygroscopic solid. The product showed an antioxidative fraction of 3.3 g/100 g of pulp. The relative abundance of the gallic/ellagic acid derivatives of 2-keto-glucono-δ-lactone in this antioxidative fraction was 30–36%.

EXAMPLE 4

Example 3 was repeated except the salt concentration used was 4% instead of 1%. The product showed an antioxidative fraction of 3.5 g/100 g pulp.

EXAMPLE 5

Example 3 was repeated except the salt used was 2% potassium chloride instead of 1% sodium chloride. The product showed an antioxidative fraction of 3.1 g/100 g pulp.

EXAMPLE 6

Example 3 was repeated except the salt used was 1% magnesium chloride instead of 1% sodium chloride. The product showed an antioxidative fraction of 4.2 g/100 g pulp.

EXAMPLE 7

Example 3 was repeated except the salt solution was replaced with 1% sodium citrate/citric acid buffer solution. The product showed an antioxidative fraction of 3.9 g/100 g pulp.

USE COMPOSITIONS OF INVENTION

A. Personal Care

In use, the compositions of Examples 8–10 below suppress skin aging due to the effects of exposure to sunlight.

EXAMPLE 8

MOISTURIZING LOTION COMPOSITION

| Ingredients | % (W/W) |
|---|---|
| Part A | |
| Stearic Acid XXX | 10.0 |
| Methyl Salicylate USP | 0.5 |
| Camphor USP | 0.5 |
| PPG-5 Ceteth-10 Phosphate | 2.0 |
| Propyl Paraben | 0.1 |
| Part B | |
| Triethanolamine | 2.0 |
| PPG-12 PEG-50 Lanolin | 2.0 |
| CAPROS | 0.5 |
| Deionized Water | 82.3 |
| Methyl Paraben | 0.1 |
| | 100.00 |

Procedure

Combine ingredients of Part A with mixing and heat to 80–85° C. Combine ingredients of Part B with mixing and heat to 80–85° C. Add Part B to Part A with mixing and cool to desired fill temperature.

EXAMPLE 9

WATER-IN-OIL COLD CREAM

| Ingredients | % (W/W) |
|---|---|
| Part A | |
| Mineral Oil and Lanolin Alcohol | 5.0 |
| Lanolin Alcohol NF | 1.9 |
| Aluminum Stearate, #22 | 0.1 |
| Microcrystalline Wax | 5.0 |
| Ozokerite, 170° C. MP | 2.5 |
| Mineral Oil, 70 ssu | 16.4 |
| Part B | |
| Glycerin | 1.5 |
| CAPROS | 0.1 |
| Magnesium Sulfate | 0.7 |
| Deionized Water | 65.8 |
| Part C | |
| Germaben II (1) | 1.0 |
| | 100.00 |

Procedure

Combine ingredients of Part A with mixing and heat to 70° C. Combine ingredients of Part B with mixing and heat to 70–75° C. Add Part B to Part A with mixing and cool to 40° C. Add Part C with mixing and cool to desired fill temperature.

EXAMPLE 10

SKIN REJUVENATING (O/W) LOTION

| Ingredients | % (W/W) |
|---|---|
| Phase A | |
| Polyglyceryl-3 Methyl Glucose Distearate | 3.50 |
| Glyceryl Stearate, PEG-100 Stearate | 2.50 |
| Dicapryl ether | 5.00 |
| Coco-Caprylate/Caprate | 5.00 |
| Propylene Glycol Dicaprylate/Dicaprate | 3.00 |
| Almond Oil | 2.00 |
| Cetyl alcohol | 1.50 |
| CAPROS | 2.00 |
| Phase B | |
| Glycerin | 3.00 |
| Propylene glycol | 3.00 |
| Allantoin | 0.20 |
| Methylparaben | 0.15 |
| Water, deionized | q.s. |
| Phase C | |
| Phenoxyethanol and Isopropylparaben and Isobutylparaben and Butylparaben | 0.50 |
| | 100.00 |

Procedure

Combine A, stir and heat to 65° C. Combine B, stir and heat to 65° C. Add A to B while stirring. Homogenize at moderate speeds to avoid foaming, while allowing mixture temperature to cool to 40° C. Add C, homogenize. Stir gently until mixture is homogeneous.

Example 11 below illustrates the effectiveness of the blend of the invention in enhancing the activity of sunscreen formulations.

EXAMPLE 11

SUNSCREEN O/W SPRAY-LOTION ESTIMATED SPF 25

| Ingredients | % (W/W) |
|---|---|
| Phase A-1 | |
| Propylene Glycol Isoceteth-3 Acetate | 5.00 |
| Octyl methoxycinnamate | 7.50 |
| Benzophenone-3 | 3.00 |
| Homomenthyl Salicylate | 7.00 |
| Steareth-2 | 0.40 |
| Steareth-10 | 0.80 |
| Acrylates/$C_{10-30}$ Alkyl Acrylate Crosspolymer | 0.18 |
| Synthetic Wax | 0.80 |
| Dimethicone | 1.00 |
| CAPROS | 0.25 |
| Phase B | |
| Demineralized water | 50.0 qs |

-continued

| Ingredients | % (W/W) |
|---|---|
| Phase C | |
| Demineralized water | 19.82 |
| Phenylbenzimdazole sulfonic acid | 1.00 |
| Propylene glycol | 2.00 |
| Triethanolamine | 0.90 |
| Propylene Glycol and DMDM Hydantoin ad Methylparaben | 1.00 |
| | 100.00 |

Procedure

Combine A, stir and heat to 80° C. Heat B to 80° C. Add A to B while stirring with a propeller mixer. Continue stirring A/B for 20 minutes while maintaining the temperature between 70–75° C. Combine C, heat and stir to 45° C. until dissolved. Add C to A/B with agitation. Qs water. Gently homogenize A/B/C allowing mixture to cool to room temperature. Adjust pH to 7.1–7.3 with TEA. Use high shear spray device to dispense.

B. Pharmaceutical and Nutritional Supplements

EXAMPLE 12

CAPROS TABLETS AND CAPSULES

| | Ingredient | Composition (w/w, in %) | Quantity per tablet (mg) |
|---|---|---|---|
| 1. | CAPROS | 60.0 | 250.0 |
| 2. | Avicel pH 101 | 20.0 | 84.0 |
| 3. | Starch 1500 | 17.5 | 75.5 |
| 4. | Steric acid, N.F. (powder) | 2.0 | 8.5 |
| 5. | Cab-O-Sil | 0.5 | 2.0 |

Note: CAPROS is granulated with starch paste to make it a free-flowing powder. Blend all the ingredients, except 4, for 25 min. in a blender. Screen in 4 and blend for an additional 5 min. Compress into tablets using 7/16-in standard concave tooling. Alternately, the blended material can be filled into appropriate capsules.

EXAMPLE 13

CHEWABLE CAPROS TABLETS

| | Ingredient | Composition (w/w, in %) | Quantity per tablet (mg) |
|---|---|---|---|
| 1. | CAPROS | 12.26 | 27.60 |
| 2. | Sodium ascorbate, USP | 36.26 | 81.60 |
| 3. | Avicel pH 101 | 17.12 | 38.50 |
| 4. | Sodium saccharin, (powder), N.F. | 0.56 | 1.25 |
| 5. | DiPac | 29.30 | 66.00 |
| 6. | Stearic acid, N.F. | 2.50 | 5.60 |
| 7. | Imitation orange Flavor | 1.0 | 2.25 |
| 8. | FD & C Yellow #6 dye | 0.5 | 1.12 |
| 9. | Cab-O-Sil | 0.5 | 1.12 |

Blend all the ingredients, except 6, for 20 min in a blender. Screen in 6 and blend for an additional 5 min. Compress into tablets using 7/16-in standard concave tooling.

EXAMPLE 14

"MAINTENANCE" MULTIVITAMIN TABLETS AND CAPSULES

| Ingredient | Composition (w/w, in %) | Quantity per tablet (mg) |
|---|---|---|
| 1. Vitamin A acetate (dry form 500 IU and 500 $D_2$ per mg) | 5.5 | 11.0 |
| 2. Thiamine mononitrate, USP | 0.8 | 1.65 |
| 3. Riboflavin, USP | 1.1 | 2.10 |
| 4. Pyridoxine HCl, USP | 1.0 | 2.10 |
| 5. 1% Cyanocobalamine (in gelatin) | | |
| 6. D-Calcium pantothenate, USP | 3.75 | 7.50 |
| 7. CAPROS, free-flowing | 33.25 | 66.50 |
| 8. Niacinamide | 11.0 | 22.00 |
| 9. DiTab | 13.1 | 26.20 |
| 10. Microcrystalline cellulose, N.F. | 25.0 | 50.00 |
| 11. Talc, USP | 3.0 | 6.00 |
| 12. Stearic acid, (powder), N.F. | 1.5 | 3.00 |
| 13. Magnesium stearate, (powder), N.F. | 1.0 | 2.00 |

Blend all ingredients for 20 min in a suitable blender. Screen in 12 and blend for an additional 5 min. Compress at a tablet weight of 200 mg using 3/8-in standard concave tooling. Alternately, blended material is filled into a capsule containing 200 mg of multi-vitamins. These tablets or capsules can be used as nutritional supplements.

EXAMPLE 15

GERIATRIC FORMULA VITAMIN TABLETS

| Ingredient | Composition (w/w, in %) | Quantity per tablet (mg) |
|---|---|---|
| 1. Ferrous sulfate, USP 95% Ethecal granulation | 30.00 | 156.00 |
| 2. Thiamine mononitrate, USP | 1.09 | 6.00 |
| 3. Riboflavin, USP | 1.00 | 5.50 |
| 4. Niacinamide, USP | 6.00 | 33.00 |
| 5. CAPROS, free-flowing powder | 17.45 | 96.00 |
| 6. Calcium pantothenate, USP | 0.73 | 4.00 |
| 7. Pyridoxine HCl, USP | 0.14 | 0.75 |
| 8. Cyanocobalmine, 0.1% spray dried | 0.82 | 4.50 |
| 9. AcDisol | 2.00 | 11.00 |
| 10. Stearic acid, (powder), N.F. | 2.00 | 11.00 |
| 11. Magnesium stearate, (powder), N.F. | 0.25 | 1.38 |
| 12. CeloCat | 38.52 | 211.87 |

Prepare a premix of items 2, 3, 6, 7. Mix in other ingredients except 10 and 11 and blend for an additional 5 min. Compress using oval punches (1=0.480 in., w=0.220× cup=0.040 in.) Sugar or film coat.

EXAMPLE 16

GERIATRIC FORMULA VITAMIN TABLETS

Example 15 was repeated except 50% CAPROS is replaced with ascorbic acid USP fine crystal. These tablets can be used as nutritional supplements.

A Comparative Antioxidant Defense

By Em-A/-B vis-a-vis AA

A redox system was provided to compare the antioxidant defense capabilities provided by Emblicanin-A/-B (Em A/B)

and ascorbic acid (AA). The redox-activating system consisted of 2,6-dichlorophenolindo-phenol (DCPI, oxidized form) and $DCPIH_2$ (colorless, reduced form); and (i) ascorbic acid (AA); or (ii) Em-A/B. This redox system inhibits the reoxidation of $DCPTH_2$ by atmospheric oxygen. This is due to the fact, that, the interaction products of the antioxidant, Em-A/B, unlike that of AA, acted as a potent antioxidant till two-to-three successive stages of the redox reaction. This was revealed from the fact that the integrity of the reduced form of DCPI was retained for a prolonged period (>2 hours) after reduction with Em-A/B, while in case of reduction with AA, aerial/soln. Oxygen oxidation of the $DCPIH_2$ solution readily produced the colored DCPI (see Table). Also, interestingly, a 1:1 combination of AA and Em-A/B provided much better protection to the reduced form born in respect of reoxidation and polymerization (note b, Table) than Aa alone. DCPI-sodium salt in 5% aq. Metaphosphoric acid (concn. Of DCPI, 1.1 mM); AA (1.25 mM), and Em-A/B (1.25 mM), and a 1:1 combination of Am-A/B (0.625+0.625 mM), in water, were used. In a typical experiment, the reductaness; in water, were added dropwise to the DCPI-Na soln till the color was discharged. Then a few more drops of the reductant was added to the colorless soln. The time dependent regeneration of DCI was monitored by HPTLC (reflectance spectra, the calculation of areas of the products was done from standard curves). Independently, the quantification of the products ratios was done by visible spectrophotometry (Beckmann DU-66) at lambda 595–602 nm (for DCPI) and 530–550 nm (broad band) for $DCPIH_2$. The results are given below. Inhibition[a] of reoxidation of $DCPIH_2$ by antioxidants, AA and Em-A/B

| Group/treatment | Relative amounts of $DCPI:DCPIH_2$ in soln at time (hr) | | | |
| --- | --- | --- | --- | --- |
| | 0.1 | 1 | 2 | 8 |
| 1. Control (DCPI) | 100 | 100 | 100 | 100 |
| 2. DCPI + AA (1.25 mM) | 0:100 | 80:10[b] | 75:0[b] | 65:0[b] |
| 3. DCPI + Em – A/B (1.25) | 40:60[a] | 0:100 | 0:100 | 50:10[b] |
| 4. DCPI + AA + Em – A/B (0.625 + 0.625) | 5:95 | 10:85 | 20:60[b] | 50:10[b] |

[a]Mean of ten replicates;
[b]the remaining compounds are baseline polymeric products (HPTLC);
[c]there was a short lag-period (quiescent) before Em – A/B can reduce DCPI.

Radical Captodative Action of Em-A/B Most research in the field of auto-oxidation is concerned with developing chemicals which, when added in small quantities to a free-radical generating/susceptible compound, react rapidly with the incipient free radicals of an auto-oxidation chain and stop it (by captivating) from progressing. The normal mechanism of captodative action of naturally occurring phenolics is mimicked by BHT (2,6-di-tert-butyl-4-methylphenol). BHT reacts with two molecules of peroxy radicals (ROS) and converts them to much less damaging products. Em-A/-B was found to be 4 to 5 times more potent than either BHT or BHA. This is because the low molecular weight galloellagi tannoids, coupled with reductions (2-ketogluconolactone and equivalents), acts by reviving the activity of the reductant via addition of H in several successive redox stages (di, tri oligomeric tannoids); and they have been found to be one of the best quenchers for oxygen free radicals (ROS). The rate constant for Em-A/B for quenching singlet oxygen ($^1O_2$) was $8.5 \times 10^8$ (in methanol). When complexed with lecithin, the complex, by way of facile partition into lipophilic membranes of cells, functions more efficiently, in vivo, as an antioxidant-free radical captodative agent. Conjugated polyoxygenated flavonols, in CAPROS, (e.g. Rutin) offer synergistic action as secondary antioxidant agents. The activity is attributed to their ability to donate H atoms (from 3',4'and other phenolic OH positions) to peroxy radicals to make them inactive. Quercetin, at $5 \times 10^{-5}$ M concentration, inhibited 70% of the perchromate initiated peroxidation of rat liver mitochondria (quercetin is the de-glycosylated aglycone of rutin). Rutin, at a $2.5 \times 10^{-5}$ M concn, inhibited (50%) of the enzymes 5-lipoxygenase and prostaglandin synthetase. Hence, the presence of Rutin, along with Em-A/B, augments the antioxidative-radical captodative actions of CAPROS.

Inhibition of Lipid Peroxidation

Lithium salt of β-elaeostearic acid (ESA) was dissolved in ethanol and 1% (w/w) antioxidants, namely, CAPROS™, vitamin C and a blend of vitamin C/E (1:30, w/w) in polyethylene glycol, were added to this solution. The changes in the integrity of ESA were monitored by HPTLC [CAMAG, TLC Scanner II, CATS version 3.14 software; quenching mode; wavelength 254 nm; precoated silicagel plates, Merck 60 F 254; solvent system hexanediethylelther:99.5:0.5].

CAPROS at the end of 3-months still produced protection to ESA from polymerization to the extent of about 70%. Vitamin C, on the other hand, completely lost its protective effect to ESA within 7 days. Vitamin C & E blend, also, at the end of 7 days exhibit protection to ESA by about 15%. Thus, the protective antioxidant effect of CAPROS is much more than the recognized antioxidants, such as, vitamin C and a blend of vitamin C/E.

Emblicanin-A/B Complex with Lecithin (Emblisome)

Skin aging is known to be strongly triggered by free radicals arising from sunlight, especially in the range UV-A and UV-B radiation. A compound able to capture and inactivate the reactive oxygen species (ROS), arising out of radiation, could prevent the damaging effect of UV light on skin. Thus, UV erythema was chosen as a parameter for radiation protective action of Em-A/B.

Preparation Of Emblisome

Emblicanin-A/B (1 mM) was stirred with dipalmitoyl-phosphatidycholine (1 mM), in n-heptane (100 ml), for 30 min. The solvent was evaporated in vacuum. The formation of the complex was established by HNMR spectroscopy and its solubility in aprotic associations/solvents. An aqueous gel containing 5% Emblisome, in micellar form (by Scanning Electron Microscopy) showed in human volunteers (after the usual tolerability test, lack of irritation, skin sensitization) the maximum protective effect. In this dose, Emblisome provided a 50% reduction of the UV evoked erythema as compared to a placebo. The 5 human volunteers, in each group, were treated immediately after a 2–4 min radiation at 1.5 Rad; with a 0.5 ml of aqueous gels of Emblisome, containing 0.5, 2.5 and 5% Emblisome or the placebo. The intensity of the redness with and without Emblisome treatment were evaluated both subjectively in arbitrary units and objectively by means of a chromometer. Prior application of the gel (5%), provided complete protection for all against UV radiation-induced skin affliction.

Prevention of DNA Strand Scission

The DNA strand scission was investigated by a method published by T. Ozawa, et al [*Biochem. Mol. Biol. Int.* 31, 455–46, 1993]. The method consists of addition of hydrogen peroxide (30%, final concentration 25 mM) to a mixture of $Cu(en)_2$ (final concentration 0.25 mM) and 0.5 mcg of PBR 322 plasmid DNA solution (Takara Co., Japan). The hydroxyl radical, generated from $Cu(en)_2$-hydrogen peroxide reaction, caused DNA strand scission.

At physiological pH, CAPROS significantly suppressed the DNA strand-scission by hydroxyl radicals produced from the reaction of Cu(en)$_2$ and hydrogen peroxide. Both vitamin C and a blend of vitamin C/E (1:30), w/w) accelerated DNA strand-scission compared to the control value (Table 1). The protective effect of CAPROS is due to: (1) Captodative action on the generation of hydroxyl radical by chelation of Cu ions from Cu(en)$_2$-complex. In contrast, both vitamin C and a blend of vitamin C/E produced lose and partially chelated Cu ions, which, by Udenfriend-type reaction, further accelerated the DNA strand-scission (Table 1). The importance of DNA strand-scission in cellular damage is well known. CAPROS helps to maintain the integrity of DNA against oxidative stress. It is well documented that vitamin E, also under certain conditions, acts as a prooxidant. Hence, the augmentation of DNA strand-scission (instead of protection) by vitamin C/E blend is self-explanatory.

TABLE 1

Comparative Suppressive Effects of DNA Strand Scission

| TYPES OF DNA | 1 | 2 | 3 | 4 | 5 |
|---|---|---|---|---|---|
| Native form of Supercoiled DNA (SC) | 90 | — | 80 | 5 | — |
| Open circular form Of DNA (OC) | 10 | 60 | 20 | 65 | 40 |
| Linear form of DNA (LIN, Produced after breakage) | — | 40 | — | 30 | 60 |

1. DNA alone (without OH radical). Note: LIN absent and OC is intermediate to LIN
2. DNA + OH radical [from Cu(en)$_2$-hydrogen peroxide)
3. DNA + OH radical + CAPROS. Note: LIN absent and OC is only 20%
4. DNA + OH radical + vitamin C/E blend. Note: Depletion of SC concentration
5. DNA + OH radical + vitamin C. Note: Significant increase in LIN value indicative of DNA strand scission.

Stability of Ag. Soln of CAPROS

CAPROS (ca. 1%) soln. was kept at room temperature in a sealed bottle for 6 months. The transformation of its small tannoid constituents into medium molecular weight (also antioxidants) was only 20–25% (as determined by HPTLC). This indicated that CAPROS, in solution, was much more stable than commercially available antioxidants such as AA and magnesium ascorbyl phosphate.

While the invention has been described with particular reference to certain embodiments thereof, it will be understood that changes and modifications may be made which are within the skill of the art. Accordingly, it is intended to be bound only by the following claims, in which:

What is claimed is:

1. A process for producing an antioxidant blend from *Emblica officinalis* fruit comprising extracting the finely pulped fruit with a dilute aqueous or alcoholic-water salt solution at a temperature of about 70° C.±5° C. to form an extract-containing solution, filtering, and drying to provide the desired antioxidant blend as a powder.

2. A process according to claim 1 wherein the dilute aqueous salt solution is a 0.1 to 5% solution of sodium chloride, potassium chloride, calcium chloride or magnesium chloride.

3. A process according to claim 1 wherein the dilute aqueous salt solution is a 0.1 to 5% buffered solution of sodium citrate/citric acid, sodium acetate/acetic acid or sodium phosphate/phosphoric acid.

4. A process according to claim 1 wherein drying is carried out by spray-drying or vacuum-drying.

5. A process according to claim 1 wherein the yield of the antioxidant blend is about 1 to 5% by weight of the pulp.

6. A process according to claim 1 wherein the antioxidant blend consists essentially of, by weight, (1) and (2) about 35–55% of the gallic/ellagic acid derivatives of 2-keto-glucono-δ-lactone; (3) about 4–15% of 2,3-di-O-galloyl-4,6-(S)-hexahydroxydiphenoylgluconic acid; (4) about 10–20% of 2,3,4,6-bis-(S)-hexahydroxydiphenoyl-D-glucose; (5) about 5–15% of 3',4',5,7-tetrahydroxyflavone-3-O-rhamnoglucoside; and (6) about 10–30% of tannoids of gallic/ellagic acid.

7. An antioxidant blend obtained by the process of claim 1.

8. An antioxidant blend consisting essentially of, by weight, (1) and (2) about 35–55% of the gallic/ellagic acid derivatives of 2-keto-glucono-δ-lactone; (3) about 4–15% of 2,3-di-O-galloyl-4,6-(S)-hexahydroxydiphenoyl-gluconic acid; (4) about 10–20% of 2,3,4,6-bis-(S)-hexahydroxydiphenoyl-D-glucose; (5) about 5–15% of 3',4',5,7-tetrahydroxyflavone-3-O-rhamnoglucoside; and (6) about 10–30% of tannoids of gallic/ellagic acid.

9. A personal care, pharmaceutical or nutritional composition including the antioxidant blend of claim 8.

10. A composition according to claim 9 which contains about 0.05 to about 10% by wt. of said blend.

11. A skin care composition according to claim 9 in the form of a lotion, cream or gel.

12. A pharmaceutical composition according to claim 9 in the form of a tablet, syrup, elixir or capsule.

13. A nutritional composition according to claim 9 which contains about 0.05 to 5% of said blend.

* * * * *